United States Patent [19]

Dickhudt et al.

[11] Patent Number: 4,770,328
[45] Date of Patent: Sep. 13, 1988

[54] TISSUE STIMULATOR CASING

[75] Inventors: Eugene A. Dickhudt, New Brighton; Michael Krol, Golden Valley, both of Minn.

[73] Assignee: Medtronic, Inc., Minneapolis, Minn.

[21] Appl. No.: 450,329

[22] Filed: Dec. 16, 1982

[51] Int. Cl.⁴ .................................................. A45F 5/00
[52] U.S. Cl. .................................... 224/252; 206/305; 128/419 P
[58] Field of Search ............... 150/52 J; 206/305, 387; 224/252, 904, 902; 128/421, 422, 419 P

[56] References Cited

U.S. PATENT DOCUMENTS 2,548,201  4/1951  Cromley ............................. 224/252
4,347,849  9/1982  Congdon ........................ 128/419 P Primary Examiner—Henry J. Recla
Assistant Examiner—David Voorhees
Attorney, Agent, or Firm—Robert J. Klepinski; Joseph F. Breimayer; John L. Rooney

[57] ABSTRACT

A casing for a tissue stimulator includes a box portion for containing the stimulator circuitry and a cover hingeably mounted on the box portion. The cover has a clip for mounting on the user's belt. The box rotates away from the cover approximately 90° to a generally horizontal position wherein the user can manipulate controls on the stimulator.

2 Claims, 1 Drawing Sheet

U.S. Patent  Sep. 13, 1988  4,770,328
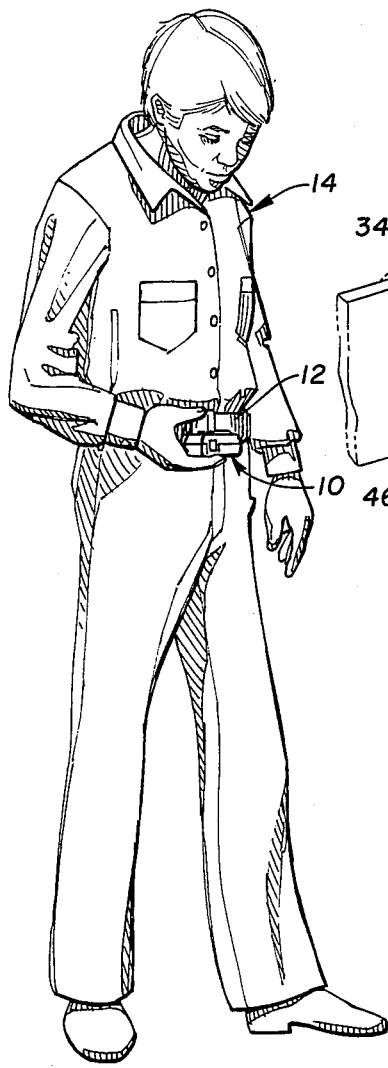
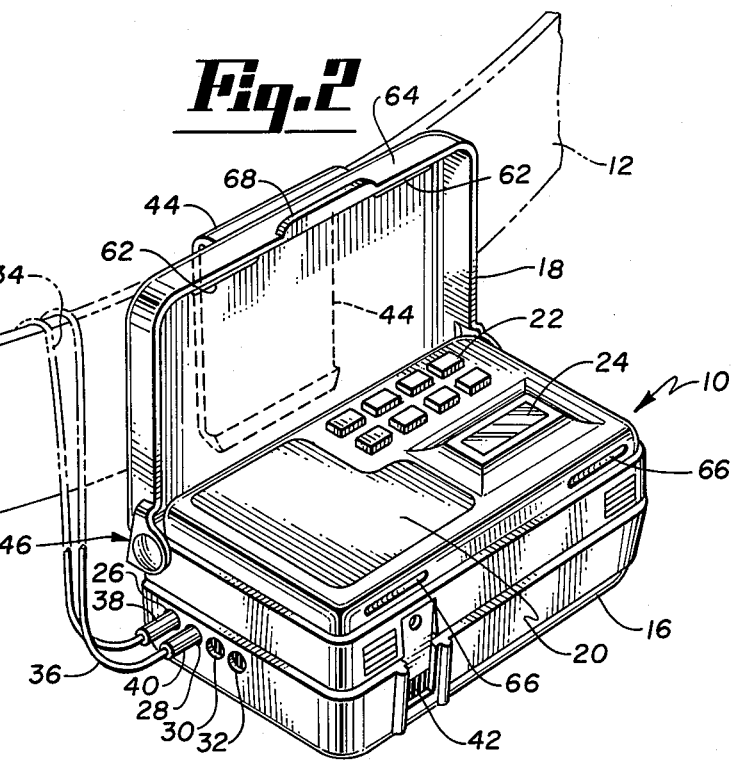
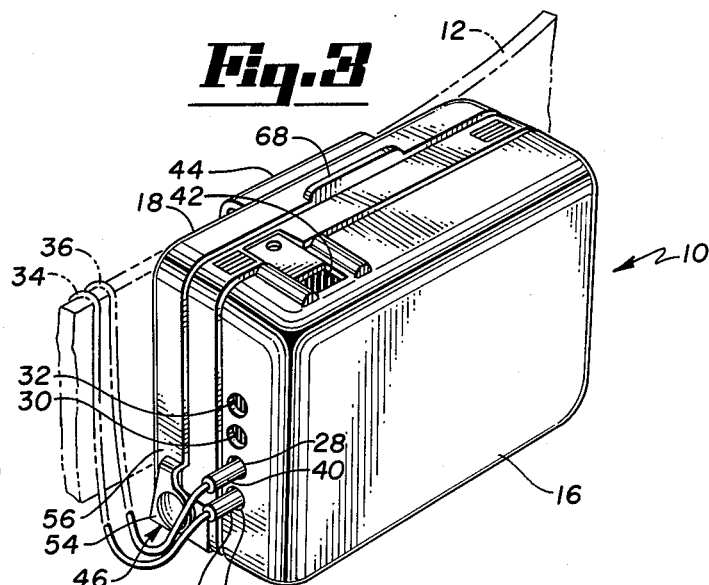
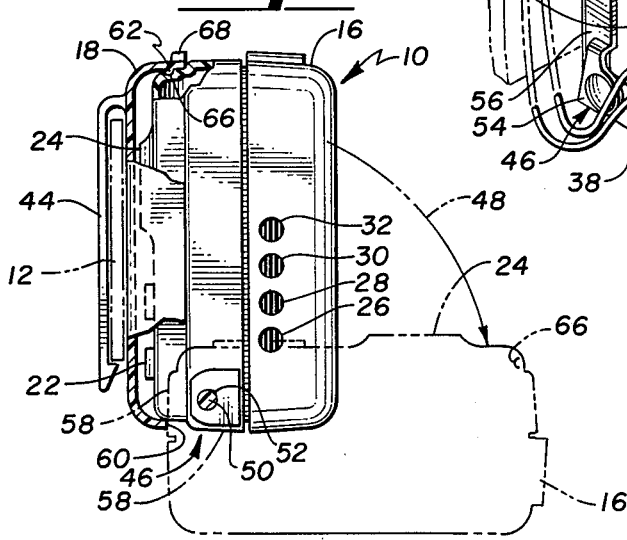
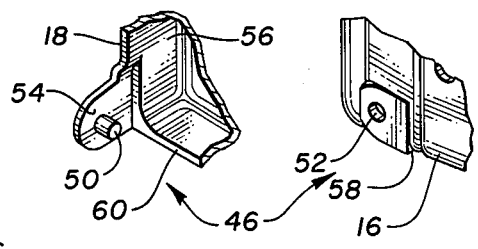

4,770,328

TISSUE STIMULATOR CASING

BACKGROUND OF THE INVENTION

1. Field of the Invention

This invention relates to casings for electronic medical devices, particularly those casings which provide protection for tissue stimulator controls.

2. Prior Art

Users of tissue stimulators, such as transcutaneous electronic nerve stimulators (TENS), often wear the stimulator attached to their clothing so that stimulation can occur during normal activity. In fact, in many cases, it is this stimulation which eases pain sufficiently to allow normal activity. One common technique for attachment of a stimulator is to provide a clip on a stimulator housing which the user can attach to his belt.

A pair of electrodes, or in some cases, two pair of electrodes, are attached to the user's skin. Lead wires then extend from the nerve stimulator, under the clothing, into the electrodes. One method is to run the lead wires over the belt and then inside the pants or shirt of the user. Very little of the lead wire is then visible during normal activity, so that the use of the device is not particularly obtrusive.

While the wearable tissue stimulator allows constant stimulation during normal activity, it is difficult to adjust and monitor without removal from the user's clothing. In order to check on the amplitude of the present stimulation, for example, the user must remove the device, check the setting, and then reattach it. In order to allow this movement, slack lead wire must be provided. Some users coil this slack wire and place it inside the belt. The excess wire is bulky and difficult to conceal under the clothing.

The prior art tissue stimulators do not provide a casing which allows easy manipulation of the stimulator controls without removal from the person, while protecting the controls from accidental activation.

SUMMARY OF THE INVENTION

A casing for an electronic medical device such as a tissue stimulator includes a first casing portion for partly containing the medical device and a second casing portion shaped to mate with the first casing portion to form a complete casing. Attachment means are provided for attaching the second casing portion to a user of the medical device. The attachment means is preferably a belt clip.

Connecting means connect the first casing portion to the second casing portion so that the two portions are movable relative to each other from a first closed position in which the portions are mated to protect the medical device and a second open position in which the medical device is accessible to the user.

In the preferred embodiment, the first casing portion is a box for containing a tissue stimulator. The second casing portion is a cover which is hingeably mounted to the box.

A latch means is preferably provided for holding the box and cover in the first closed position.

A stop means is provided to stop the relative movement of the first and second casing portions at a fixed angle in the second position. The fixed angle is preferably 90°.

BRIEF DESCRIPTION OF THE DRAWINGS

FIG. 1 is a perspective view of a tissue stimulator user with a tissue stimulator constructed according to the present invention mounted on his belt in an open position;

FIG. 2 is an enlarged perspective view of the tissue stimulator of FIG. 1;

FIG. 3 is a perspective view of the tissue stimulator of FIG. 2 shown in a closed position;

FIG. 4 is a side elevational, partially cutaway, view of the tissue stimulator of FIG. 3, with the open position shown in phantom;

FIG. 5 is an enlarged fragmentary view of a pin of a hinge of the tissue stimulator of FIG. 3; and FIG. 6 is an enlarged fragmentary view of the socket of the hinge of the tissue stimulator of FIG. 3.

DETAILED DESCRIPTION OF THE PREFERRED EMBODIMENTS

The present invention is illustrated embodied in a tissue stimulator 10 which is shown mounted on a belt 12 of a user 14. Tissue stimulator 10 is shown in its first or open position, wherein user 14 is monitoring the stimulator 10.

Tissue stimulator 10 includes a first casing portion or rectangular box 16 and a second casing portion or cover 18, which are constructed of suitably resilent and protective material such as high-impact plastic. In the example illustrated, box 16 and cover 18 are constructed of the same material. In this embodiment, box 16 contains the pulse generator circuitry (not shown) of the tissue stimulator. On one surface 20 of the box 16 are mounted user controls 22 and a display 24. User controls 22 includes a keyboard or control switches to control parameters of the stimulation provided by tissue stimulator 10, such as pulse amplitude or pulse rate. Display 24 is a human-readable display, such as an LCD display to provide indications of the current settings of the output pulse parameters.

Box 16 includes output jacks 26, 28, 30, and 32 mounted on a side wall 33. Jacks 26 and 28 form a pair to provide output for a first channel of tissue stimulator 10. Jacks 30 and 32 form a pair to provide output for a second channel. Leads 34 and 36 are connected to jacks 26 and 28 by plugs 38 and 40 respectively. Leads 34 and 36 provide current to body electrodes (not shown) which stimulate the tissues of user 14.

Box 16 and cover 18 meet to form a unified tissue stimulator casing when tissue stimulator 10 is in its second or closed position, as shown in FIG. 3.

A sliding on/off switch 42 is provided on box 16 in a position which is accessible to user 14 whether box 16 and cover 18 are in the open or closed position.

Means are provided on cover 18 to attach tissue stimulator 10 to user 14. In the embodiment illustrated, the means for attaching consist of a clip 44 which mounts over belt 12.

Box 16 and cover 18 are connected by means of a hinge 46, and move relative to each other from the closed position illustrated in FIG. 3 to the open position illustrated in FIG. 2 by rotation along an axis of hinge 46. The range of movement is illustrated by arrow 48 in FIG. 4. The hinge 46 of the embodiment illustrated consists of a pin 50 at each end of a lower edge of cover 18.

Each pin 50 fits into a corresponding socket 52 in the side of box 16, near its lower edge. Each pin 50 is mounted on an ear 54 which projects from a wall 56 of cover 18. Rotational movement of pin 50 within socket 52 provides for movement of box 16 upon a longitudinal axis through the two pins 50.

Ears 54 are preferably slightly flexible so that they may be bent outward to remove pins 50 from sockets 52 in case user 14 wishes to remove cover 18 from box 16.

The movement of box 16 relative to cover 18 is preferably limited so that box 16 rests in the open position shown in FIG. 4, where an angle between box 16 and cover 18 is illustrated by arrow 48. This angle is preferably approximately 90°. At this angle, user 14 can comfortably look down at display 24 and easily manipulate the controls 22.

The movement of box 16 relative to cover 18 is stopped by contact of a back wall 58 of box 16 with butting edge 60 of cover 18, as best illustrated in FIG. 4. Of course, many acceptable hinge and stop combinations may be designed by one skilled in the art. The preferred embodiment illustrated is shown because of its simplicity, durability, and removability.

Tissue stimulator 10 is retained in its closed position as illustrated in FIG. 3, by latch means which include a pair of bosses 62 which project downward from a top wall 64 of cover 18 and mate with a pair of grooves 66 provided in a top wall of box 16. The partially cutaway view of FIG. 4 illustrates the projection of boss 62 into groove 64 when tissue stimulator 10 is in its closed position. A finger catch 68 is provided to assist user 14 in separating cover 18 from box 16.

A tissue stimulator 10 constructed according to the present invention provides many advantages over prior art stimulators. First, stimulator 10 can be monitored and operated using only one hand as illustrated in FIG. 1. The prior art method of removing the stimulator from one's belt with one hand and then manipulating the controls with the other hand is greatly simplified. This makes the use of stimulator 10 easier during periods of normal activity. It also assists those that have limited mobility in one hand.

A second major advantage of a tissue stimulator 10 constructed according to the present invention is that it eliminates the bulky coil of slack lead wire that formerly had to be concealed under the clothing. In the example illustrated, the jacks 26 and 28 which receive leads 34 and 36 move only approximately an inch between the open and closed positions of tissue stimulator 10. Therefore, there is no need for a great amount of slack in leads 34 and 36. Once leads 34 and 36 are comfortably situated on the body and are attached to electrodes, there is no need for extra lead wire in the vicinity of tissue stimulator 10.

The present invention also provides a durable and safe protective cover for the keyboard 22 and display 24 of tissue stimulator 10. When tissue stimulator 10 is in its closed position, keyboard 22 and display 24 are protected from accidental actuation and from damage due to contact with furniture or other external articles. This invention eliminates the possibility that user 14 will forget to close the protective cover over keyboard 22 or display 24. The movement of first casing portion 16 to its closed position automatically insures that the keyboard 22 and display 24 will be protected.

Although the present invention has been described in terms of a preferred embodiment of a tissue stimulator, it is to be understood that those skilled in the art can substitute other designs in the practice of the present invention, as well as practice the invention with other electronic medical equipment. The embodiment is described for illustrative purposes, and not to define the broadest limits of the present invention.

What is claimed is:

1. A body-wearable electrical tissue stimulator for use in conjunction with lead wires and electrodes comprising:

electrical circuitry for producing tissue stimulation signals;

a box for containing the electrical circuitry;

user controls mounted on a surface of the box and operably connected to the electrical circuitry;

a cover hingeably mounted to the box having a first closed position which the cover encloses the user controls and a second position in which the cover is swung away from the box to allow access to the user controls;

attachment means for attaching the cover to the user of the tissue stimulator; and lead-wire-accepting terminals mounted on the box and electrically connected to the electrical circuitry, the terminals being positioned on the box so that when the cover is in its first closed position the terminals are in a first location and when the cover is in its second open position the terminals are in a second location, the first and second location being generally equadistant from the body of the user.

2. The tissue stimulator of claim 1 wherein the attachment means mounts on a belt worn by the user and the box swings away from the user to an angle of approximately 45 degrees to the cover when in the second open position.

* * * * *